United States Patent [19]

Clark et al.

[11] 4,364,956
[45] Dec. 21, 1982

[54] 5-SUBSTITUTED PYRANONE COMPOUNDS AND THEIR USE AS PHARMACEUTICALS TO TREAT AN IMMEDIATE HYPERSENSITIVITY CONDITION

[75] Inventors: Barry P. Clark, Fleet; William J. Ross, Lightwater; Alec Todd, Wokingham, all of England

[73] Assignee: Lilly Industries Limited, London, England

[21] Appl. No.: 303,307

[22] Filed: Sep. 17, 1981

Related U.S. Application Data

[62] Division of Ser. No. 134,387, Mar. 27, 1980, abandoned.

[30] Foreign Application Priority Data

Apr. 5, 1979 [GB] United Kingdom ............... 7912063

[51] Int. Cl.³ ............... A61K 31/34; A61K 31/35; C07D 309/32
[52] U.S. Cl. ............... 424/269; 424/283; 549/416; 549/419; 549/420; 548/251; 548/252; 548/253; 564/218; 564/341; 564/342; 564/347; 564/384
[58] Field of Search ............... 260/345.7 R, 345.8 R, 260/345.9 R; 424/269, 283; 542/441; 548/251, 252, 253; 549/416, 420, 419

[56] References Cited

U.S. PATENT DOCUMENTS 4,060,533 11/1977 Nadelson ............... 260/345.7 R
4,065,290 12/1977 Taylor ............... 564/345 X

OTHER PUBLICATIONS

Borsche et al., Ann, 453, 148 (1927).
Soliman et al., J. Chem. Soc., 1956, pp. 3663-3668.
Eiden et al., Arch. Pharm., 308, 489 (1975).
Schiefer et al., Angew. Chem. Internat. Edit. 4, 527 (1965).
Kirby et al., J. Org. Chem., 28, 2266 (1963).
Hampton et al., J. Org. Chem., 30, 4263 (1965).
Garkusha, Chem. Abstract, 63, 1458d (1965).

*Primary Examiner*—Nicky Chan
*Attorney, Agent, or Firm*—Karen B. O'Connor; Arthur R. Whale

[57] ABSTRACT

Compounds are described of the formula

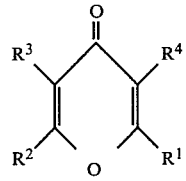

in which $R^1$ is $COOR^5$, $CONHR^5$, cyano, 5-tetrazolyl or 5-tetrazolylaminocarbonyl, where $R^5$ is hydrogen or $C_{1-6}$ alkyl; $R^2$ is hydrogen or $C_{1-6}$ alkyl; $R^3$ is a group of the formula $$R^6-(Z)_m-$$

where m is O or 1, Z is O, S, SO, $SO_2$ or CO, and $R^6$ phenyl optionally substituted by one or more group selected from halogen, $C_{1-4}$ alkyl, $C_{3-6}$ cycloalkyl, $C_{1-4}$ alkoxy, benzyloxy, hydroxy, nitro, $C_{1-4}$ alkylthio, $C_{1-4}$ alkylsulphinyl, $C_{1-4}$ alkylsulphonyl, amino and $NHR^7$ where $R^7$ is $C_{2-6}$ acyl; and $R^4$ is hydrogen, $C_{1-6}$ alkyl or halogen; and salts thereof. These compounds have pharmaceutical properties and in particular are useful in the treatment of immediate hypersensitivity conditions such as asthma.

9 Claims, No Drawings

5-SUBSTITUTED PYRANONE COMPOUNDS AND THEIR USE AS PHARMACEUTICALS TO TREAT AN IMMEDIATE HYPERSENSITIVITY CONDITION

This application is a division of application Ser. No. 134,387, filed Mar. 27, 1980, now abandoned.

This invention relates to novel pyranone compounds and their use as pharmaceuticals.

Certain pyran-4-one compounds have already been described in the literature and, for example, compounds of this general type are disclosed in Annalen 453, 148 (1927), J. Chem. Soc. 3663 (1956), Arch. Pharm. 308, 489 (1975), Angew. Chem. Internat. Edit. 4, 527 (1965) and in J. Org. Chem. 28, 2266 (1963) and 30, 4263 (1965). However, the pharmaceutical properties of these compounds have not been investigated and in none of these instances was any useful biological activity reported.

We have now discovered novel pyran-4-one compounds of a quite different chemical structure, which are useful as pharmaceuticals especially in the treatment of immediate hypersensitivity conditions.

The invention comprises a compound of formula (I)

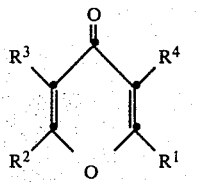

in which $R^1$ is $COOR^5$, $CONHR^5$, cyano, 5-tetrazolyl or 5-tetrazolylaminocarbonyl, where $R^5$ is hydrogen or $C_{1-6}$ alkyl; $R^2$ is hydrogen or $C_{1-6}$ alkyl; $R^3$ is a group of the formula $$R^6-(Z)_m-$$

where m is 0 or 1, Z is O, S, SO, $SO_2$ or CO, and $R^6$ is phenyl optionally substituted by one or more groups selected from halogen, $C_{1-4}$ alkyl, $C_{3-6}$ cycloalkyl, $C_{1-4}$ alkoxy, benzyloxy, hydroxy, nitro, $C_{1-4}$ alkylthio, $C_{1-4}$ alkylsulphinyl, $C_{1-4}$ alkylsulphonyl, amino and $NHR^7$ where $R^7$ is $C_{2-6}$ acyl; and $R^4$ is hydrogen, $C_{1-6}$ alkyl or halogen; and salts thereof.

When reference is made to $C_{1-6}$ alkyl or $C_{2-6}$ acyl groups it is intended to include both straight and branched chain groups, for example, methyl, ethyl, n-propyl, i-propyl, n-butyl, s-butyl, t-butyl, n-pentyl and n-hexyl, the most preferred groups being methyl and ethyl and the corresponding acyl groups derived from them. In the case where $R^1$ is $COOR^5$ and $R^5$ is alkyl, it is to be understood that substituted alkyl groups are also included and are to be regarded as equivalent, in view of the fact that it is often merely necessary to attach an ester group that readily cleaves to give the free acid, and examples of such substituted alkyls include acetoxymethyl, methylthiomethyl, methylsulphinylmethyl and methylsulphonylmethyl.

The term, halogen, refers to fluorine, chlorine, bromine or iodine, and is especially chlorine or bromine.

When reference is made to substituted phenyl, there can be one or more substituent on the nucleus, such as 1 to 3 substituents and preferably a single substituent. A $C_{3-6}$ cycloalkyl group is preferably cyclopropyl or cyclohexyl and when the substituent is $C_{1-4}$ alkoxy, $C_{1-4}$ alkylthio, $C_{1-4}$ alkylsulphinyl $C_{1-4}$ alkylsulphonyl, the $C_{1-4}$ alkyl group may be any of the examples listed above and is preferably methyl or ethyl. A group of the formula $NHR^7$ is preferably acetamido.

Included in the above general formula are the salts of compounds, for example, those in which $R^1$ is COOH or 5-tetrazolyl, or compounds in which acidic or basic groups are attached to the substituent $R^6$. The acid addition salts are preferably the pharmaceutically-acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicylic, o-acetoxybenzoic, nicotinic or isonicotinic acid, or organic sulphonic acids for example methane sulphonic, ethane sulphonic, 2-hydroxyethane sulphonic, toluene-p-sulphonic or naphthalene-2-sulphonic acid. The salts of acid compounds are preferably pharmaceutically-acceptable, non-toxic, salts of suitable mineral bases, such as alkali metal hydroxides especially the potassium or sodium salts, or alkaline earth metal hydroxides especially the calcium salts, or of organic bases such as amines. Aparts from the pharmaceutically-acceptable salts, other salts are included, such as for example, those with picric or oxalic acid; they may serve as intermediates in the purification of the compounds or in the preparation of other, for example, pharmaceutically-acceptable, salts or are useful for the purpose of identification, characterization or purification.

In the above formula (I), some of the preferred groups are those which include one or more of the following features (a) $R^1$ is $COOR^5$, $CONHR^5$ or 5-tetrazolyl
(b) $R^1$ is $COOR^5$ where $R^5$ is hydrogen or $C_{1-6}$ alkyl
(c) $R^2$ and $R^4$ are both hydrogen
(d) $R^3$ is of the formula $$R^6-(Z)_m-$$

where m is 0 or m is 1 and Z is O or CO
(e) $R^6$ is phenyl optionally substituted by 1 to 3 substituents selected from halogen, $C_{1-4}$ alkyl, methoxy, benzyloxy and hydroxy
(f) $R^4$ is hydrogen or $C_{1-6}$ alkyl One preferred group of compounds is of the following formula

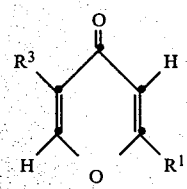

in which $R^1$ is $COOR^5$ or $CONHR^5$, where $R^5$ is hydrogen or $C_{1-6}$ alkyl, and $R^3$ is a group of the formula $R^6-(Z)_m-$ where m is 0 or 1, Z is O, S or CO and $R^6$ is phenyl optionally substituted by halogen, methyl, methoxy or hydroxy, or a salt thereof.

A further preferred group is one of formula (II) in which $R^3$ is a group of the formula $R^6-(Z)_m-$ where m is 0 or 1, Z is O or CO and $R^6$ is phenyl optionally substituted by halogen, methyl, methoxy or hydroxy.

The present invention also includes a method of preparing a compound of formula (I) which comprises reacting a compound of formula

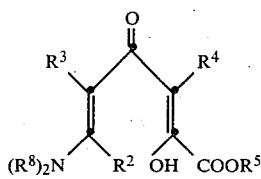

(III)

where $R^8$ is $C_{1-6}$ alkyl or $(R^8)_2N$ is a saturated heterocyclic ring such as morpholino, piperidino or pyrrolidino, with acid, optionally followed by conversion of the $COOR^5$ group into another $R^1$ substituent or by the introduction of one or more substituent in the $R^6$ group. The reaction can be carried out in both aqueous and non-aqueous conditions, preferably employing a mineral acid, such as for example hydrochloric acid or sulphuric acid, at a temperature of from 0° C. to 100° C., more especially from 10° C. to 50° C.

When it is desired to prepare a compound of formula (I) in which $R^4$ is halogen a compound of formula (III) in which $R^4$ is hydrogen can be reacted with halogen which causes liberation of hydrogen halide and ring closure to give the final halogenated product of formula (I).

Compounds of formula (III) are conveniently formed, without isolation, by reaction of a compound of formula (IV)

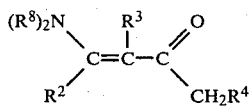

(IV)

where $R^4$ is hydrogen or $C_{1-6}$ alkyl, with a dialkyl oxalate of formula $(COOR^5)_2$ in the presence of a base. The product of this reaction may then be acidified and ring closure effected without the isolation of an intermediate of formula (III). The compounds of formula (IV) are novel and form part of this invention.

Reaction of dialkyl oxalate with a compound of formula (IV) is preferably performed in an organic solvent such as an alcoholic or ethereal solvent, for example ethanol, ether or dimethoxyethane, preferably at a temperature of from 0° C. to 100° C. The reaction requires the presence of a base such as an alkali metal alkoxide.

The intermediate of formula (IV) can readily be obtained by two alternative routes. In the first route, a ketone of formula (V)

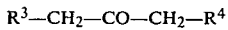

is reacted with a dialkylamide dialkylacetal of formula (VI)

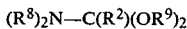

where $R^9$ is $C_{1-6}$ alkyl. The reaction is preferably carried out at a temperature in the range of from 0° C. to 100° C. The amide acetals of formula (IV) are prepared by known methods such as alkylation of amides of formula $R^2CON(R^8)_2$ with for example trialkyl oxonium fluoroborates of the formula $(R^9)_3OBF_4$, followed by treatment of the resulting complexes with alkali metal alkoxides.

The second route for preparing compounds of formula (IV) consists in acylating a compound of formula (VII)

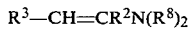

under conditions typical of acylation reactions, for example at a temperature of from 0° C. to 150° C. Suitable acylating agents are of the formula $R^4CH_2COX$ where X is halogen, especially chlorine, or $(R^4CH_2CO)_2O$. The enamines (VII) can be prepared by reacting the appropriate acetaldehyde with a dialkylamine in the presence of a base, for example potassium carbonate.

It will be appreciated that compounds prepared by the above process in which $R^1$ is $COOR^5$ where $R^5$ is hydrogen or $C_{1-6}$ alkyl can readily be converted into compounds with other $R^1$ substituents, as follows:

Compounds in which $R^1$ is $COOR^5$ where $R^5$ is $C_{1-6}$ alkyl, can be converted to the corresponding free acid in which $R^1$ is COOH by hydrolysis in the presence of acid such as a mineral acid, for example hydrochloric acid, or by reaction with boron trihalide in an inert solvent, with lithium iodide in DMF, or with sodium iodide in a mixture of methyl ethyl ketone and pyridine. Such methods are well known in the art. Conversely, compounds in which $R^1$ is $COOR^5$ where $R^5$ is $C_{1-6}$ alkyl can be prepared from the free acid by esterification of the free carboxyl group with the appropriate alcohol or by treatment with alkyl halide in the presence of base. Salts of the free acid can, of course, be prepared simply by reaction with alkali.

Compounds in which $R^1$ is $CONHR^5$ can be prepared by reacting a compound in which $R^1$ is $COOR^5$ where $R^5$ is $C_{1-6}$ alkyl, with ammonia or the appropriate amine of formula $R^5NH_2$, or they can be prepared by the reaction of ammonia or an amine of formula $R^5NH_2$ with the appropriate acyl chloride, which can in its turn be derived from the free carboxyl derivative by the reaction of thionyl chloride. Such reactions are well known in the art.

Compounds in which $R^1$ is CN can be prepared by dehydration of the amides in which $R^1$ is $CONH_2$, a convenient dehydrating agent being, for example, a mixture of triphenylphosphine and carbon tetrachloride.

Compounds in which $R^1$ is 5-tetrazolyl can be prepared by reaction of the cyano derivative prepared above with, for example sodium azide and ammonium chloride in dimethylformamide. Salts can be prepared from the 5-tetrazolyl derivatives by the addition of base according to standard techniques.

It will also be appreciated that many of the compounds of formula (I) can be converted one to another by introduction of groups into the $R^6$ nucleus employing simple and well known chemical reactions. When a nitro substituent is desired in the $R^6$ group, the unsubstituted compound can be nitrated with a mixture of concentrated nitric and sulphuric acids by conventional method. The nitro compound can subsequently be converted to other substituents such as amino or acylamino. The amino compound may be diazotised and the resultant diazonium salt converted to a variety of other products, for example, by decomposition in an alcohol to yield the corresponding alkoxy substituted compound or by reaction with a cuprous halide to yield the corresponding halo substituted compound. Hydroxy substituted compounds can be prepared from the corresponding methoxy compounds by cleavage with, for example, boron tribromide. Alkyl sulphonyl and alkyl sulphinyl substituted aryl derivatives can be prepared by oxidation of the corresponding alkylthio compound by reaction for example with m-chloroperoxybenzoic acid. Similarly when, in formula (I), Z is SO or $SO_2$, the compounds can be prepared by oxidation of the analogous thio compound.

The invention also includes a pharmaceutical composition comprising a compound of formula (I) or a pharmaceutically-acceptable salt thereof and a pharmaceutically-acceptable carrier associated therewith.

As a further feature of the invention there is included a compound of formula (I) for use as a pharmaceutical, more especially, for use in the treatment of immediate hypersensitivity conditions.

The pyranones of formula (I) and their pharmaceutically-acceptable salts, have been shown to be useful in the prophylactic and therapeutic treatment of immediate hypersensitivity diseases including asthma and in the alleviation of status asthmaticus. They are also of low toxicity.

This activity has been demonstrated in guinea pigs using either the "guinea-pig chopped lung test" described by Mongar and Schild in the Journal of Physiology (London) 131, 207 (1956) or Brocklehurst in the Journal of Physiology (London) 151, 416 (1960), or the "Herxheimer" test described in the Journal of Physiology (London) 117, 251 (1952). For example compounds have exhibited a greater than 15 percent inhibition of mediator release in the "guinea-pig chopped lung test". In the "Herxheimer" test, which is based on an allergic bronchospasm induced in guinea pigs closely resembling an asthmatic attack in man, compounds have exhibited activity at dosages ranging from 25 mg/kg to 200 mg/kg.

The compounds may be administered by various routes, although it is a special feature of the compounds that they are effective when administered orally. Thus the compounds may be administered by the oral and rectal routes, topically and parenterally e.g. by injection, being usually employed in the form of a pharmaceutical composition. Such compositions are prepared in a manner well known in the pharmaceutical art and normally comprise at least one active compound or salt of the invention in association with a pharmaceutically-acceptable carrier therefor. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material, which acts as a vehicle, excipient or medium for the active ingredient. Thus the composition can be in the form of tablets, lozenges, sachets, cachets, elixirs, suspensions, aerosols (as a solid or in a liquid medium), ointments containing for example up to 10% by weight of the active compound, soft and hard gelatin capsules, suppositories, injection suspensions and sterile packaged powders.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl- hydroxybenzoate, talc, magnesium stearate or mineral oil. The compositions of the invention may, as is well known in the art, be formulated so as to provide quick, sustained or delayed release of the active ingredient after administration to the patient.

Preferably the compositions are formulated in a unit dosage form, each dosage containing from 5 to 500 mg, more usually 25 to 200 mg, of the active ingredient. The term "unit dosage form" refers to physically discrete units suitable as unitary dosages for human subjects and animals, each unit containing a predetermined quantity of active material calculated to produce the desired therapeutic effect, in association with the required pharmaceutical carrier.

The active compounds are effective over a wide dosage range and for example dosages per day will normally fall within the range of 0.5 to 300 mg/kg and in the treatment of adult humans, more usually in the range of from 5 to 100 mg/kg. However it will be understood that the amount of the compound actually administered will be determined by a physician, in the light of the relevant circumstances including the condition to be treated, the choice of compound to be administered and the chosen route of administration and therefore the above dosage ranges are not intended to limit the scope of the invention in any way.

The following Examples illustrate the invention.

EXAMPLE 1

4-Dimethylamino-3-phenyl-3-buten-2-one

A stirred mixture of benzyl methyl ketone (26.8 ml) and dimethylformamide dimethyl acetal (30.0 ml) was heated in a distillation apparatus on an oil bath at 95°–100° C. for 1½ hours. Methanol slowly distilled off. The residual volatiles were removed under vacuum and the resulting oil was crystallised from ether-petroleum spirit (40°–60° C.) to yield the title compound (mp 66° C.).

EXAMPLES 2 TO 15

The compounds listed below were prepared by methods similar to that described in Example 1.

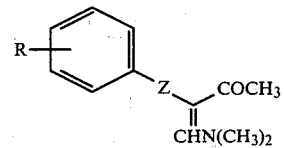

| Example | Z | R | mp °C. |
|---|---|---|---|
| 2 | — | 4-Cl | 81 |
| 3 | — | 2-CH$_3$O | 49–52 |
| 4 | — | 4-CH$_3$ | Oil |
| 5 | O | H | 99–101 |
| 6 | O | 4-Cl | 113–115 |
| 7 | O | 4-CH$_3$ | 91–93 |
| 8 | O | 4-CH$_3$O | 112–114 |
| 9 | O | 2-CH$_3$O | 142 |
| 10 | S | H | 74–76 |
| 11 | S | 4-Cl | 98–100 |
| 12 | S | 4-CH$_3$O | 74–76 |
| 13 | SO$_2$ | 4-CH$_3$ | 123–124 |
| 14 | CO | 4-Cl | 122 |
| 15 | CO | 4-CH$_3$O | 126 |

EXAMPLE 16

4-Dimethylamino-3-(4-methoxyphenyl)-3-buten-2-one

A stirred mixture of 1-(4-methoxyphenyl)-2-propanone (8.2 g) and dimethylformamide diethyl acetal (9.5 ml) was heated on an oil bath at 95°–100° C. for 30 minutes. Volatile material was removed under vacuum and the residue was crystallised from ether-petroleum spirit (40°-60° C.) to give the title compound (mp 56°-58° C.).

EXAMPLE 17

Ethyl 4-oxo-5-phenyl-4H-pyran-2-carboxylate

A solution of 4-dimethylamino-3-phenyl-3-buten-2-one (30.3 g) and diethyl oxalate (43.5 ml) in ethanol (75 ml) was added to a stirred solution of sodium ethoxide prepared by dissolving sodium (5.5 g) in ethanol (150 ml). The stirred mixture was heated under reflux for 1 hour, cooled to 20°-25° C. and acidified by addition of 5 N hydrochloric acid (150 ml). The mixture was stirred for a further hour, then cooled to 5° C., and diluted with water (300 ml). The solid title product was recrystallised from ethanol-water (mp 110°-112° C.).

EXAMPLES 18 TO 26

The compounds listed below were prepared by methods similar to that described in Example 17.

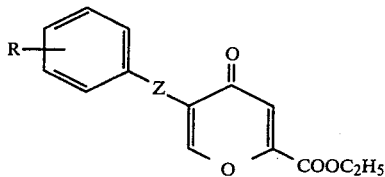

| Example | Z | R | mp °C. |
|---|---|---|---|
| 18 | — | 2-CH$_3$O | 69–71 |
| 19 | — | 4-CH$_3$ | 101–102 |
| 20 | O | H | 91–93 |
| 21 | O | 4-Cl | 127–129 |
| 22 | O | 4-CH$_3$ | 77–79 |
| 23 | S | 4-Cl | 91–92 |
| 24 | SO$_2$ | 4-CH$_3$ | 151–153 |
| 25 | CO | 4-Cl | 108–109 |
| 26 | CO | 4-CH$_3$O | 81–84 |

EXAMPLE 27

4-Diethylamino-3-phenyl-3-buten-2-one

A solution of diethylstyrylamine (1.75 g) in acetic anhydride (5 ml) was heated under reflux for an hour and then distilled under vacuum (0.02 mm) in a bulb-to-bulb apparatus (oven 150° C.). The product was crystallised from ether-petroleum spirit (40°-60° C.) at low temperature, giving crystals of the title product which melted around room temperature.

This compound was reacted with diethyl oxalate by the method described in Example 17 to give a product, ethyl 4-oxo-5-phenyl-4H-pyran-2-carboxylate, identical with that of Example 17.

EXAMPLE 28

4-Oxo-5-phenyl-4H-pyran-2-carboxylic acid

Ethyl 4-oxo-5-phenyl-4H-pyran-2-carboxylate (4.9 g) was heated with concentrated hydrochloric acid (12 ml) on a steam bath for 1½ hours. The mixture was cooled and the solid title product was recrystallised from ethyl acetate-dimethylformamide (mp 225°-227° C. with decomposition).

EXAMPLE 29

5-(4-Chlorophenylthio)-4-oxo-4H-pyran-2-carboxylic acid

A solution of ethyl 5-(4-chlorophenylthio)-4-oxo-4H-pyran-2-carboxylate (5.0 g) in dioxan (40 ml) and concentrated hydrochloric acid (20 ml) was heated under reflux for 2 hours then evaporated under vacuum. The solid residue was dried and recrystallised from ethyl acetate-petroleum spirit (60°-80° C.) to give the title product (mp 165°-167° C. with decomposition).

EXAMPLE 30

5-(4-Methylphenylsulphonyl)-4-oxo-4H-pyran-2-carboxylic acid

This compound was prepared by the method described in Example 29 (mp 210° C. with decomposition).

EXAMPLE 31

5-(4-Methoxyphenyl)-4-oxo-4H-pyran-2-carboxylic acid

Ethyl 5-(4-methoxyphenyl)-4-oxo-4H-pyran-2-carboxylate (mp 121°-123° C.) was prepared by the method described in Example 17 and hydrolysed by the method described in Example 29 to give the title product (mp 232°-234° C. with decomposition).

EXAMPLE 32

5-(2-Methoxyphenoxy)-4-oxo-4H-pyran-2-carboxylic acid

Ethyl 5-(2-methoxyphenoxy)-4-oxo-4H-pyran-2-carboxylate (mp 74°-76° C.) was prepared by the method described in Example 17 and hydrolysed by the method described in Example 29 to give the acid title product (mp 202°-203° C.).

EXAMPLE 33

4-Oxo-5-phenylthio-4H-pyran-2-carboxylic acid

Ethyl 4-oxo-5-phenylthio-4H-pyran-2-carboxylate (mp 79°-81° C.) was prepared by the method described in Example 17 and hydrolysed by the method described in Example 29 to give the acid title product (mp 178°-181° C.).

EXAMPLE 34

Propyl 5-(4-methoxyphenylthio)-4-oxo-4H-pyran-2-carboxylate

Ethyl 5-(4-methoxyphenylthio)-4-oxo-4H-pyran-2-carboxylate (mp 90°-92° C.) was prepared by the method described in Example 17 and hydrolysed to the acid (mp 190°-193° C.) by the method described in Example 29. A solution of this acid (5.4 g) in carbon tetrachloride (50 ml), n-propanol (2.9 ml) and triethylamine (2.7 ml) was heated under reflux for 7 hours, cooled, washed with dilute hydrochloric acid, then with sodium carbonate solution, dried and evaporated. The residue was crystallised from ethyl acetate-petroleum spirit (60°-80° C.) to give the title product (mp 91°-93° C.).

EXAMPLE 35

N-Methyl-4-oxo-5-phenyl-4H-pyran-2-carboxamide

A stirred suspension of 4-oxo-5-phenyl-4H-pyran-2-carboxylic acid (4.3 g) in dry benzene (50 ml) and thionyl chloride (10 ml) was heated under reflux for 12 hours. The clear solution was diluted with petroleum spirit (60°–80° C.) (50 ml) and cooled to give crystals of the acid chloride (mp 175° C.).

A solution of methylamine (0.338 g) in dry pyridine (4.5 ml) was added to a stirred, cooled suspension of the acid chloride (2.5 g) in dry pyridine (15 ml). The solution was stirred at room temperature for an hour, then cooled and diluted with water (50 ml). The solid title product was dried and recrystallised from chloroform-petroleum spirit (60°–80°) (mp 196°–198° C.).

EXAMPLES 36 AND 37

The compounds listed below were prepared by methods similar to that described in Example 35.

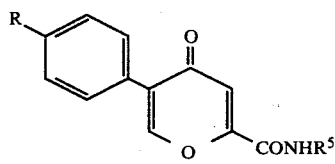

| Example | $R^5$ | R | mp °C. |
|---|---|---|---|
| 36 | $CH_3$ | $CH_3O$ | 182–184 |
| 37 | $n-C_4H_9$ | H | 157–160 |

EXAMPLE 38

4-Oxo-5-phenyl-N-(5-tetrazolyl)-4H-pyran-2-carboxamide

A stirred suspension of 5-aminotetrazole hydrate (0.9 g) in benzene (50 ml) was heated under a Dean and Stark water trap until no further water distilled off. The mixture was cooled and filtered and the solid was immediately dissolved in dry pyridine (20 ml). Solid 4-oxo-5-phenyl-4H-pyran-2-carboxylic acid chloride (2.0 g, prepared as described in Example 35) was added in portions to the cooled, stirred pyridine solution. The mixture was stirred for 2 hours at room temperature, cooled and diluted with water (50 ml). The solid title product was recrystallised from dimethylformamide (mp > 300° C.).

EXAMPLE 39

N-Butyl-4-oxo-5-phenoxy-4H-pyran-2-carboxamide

Ethyl 4-oxo-5-phenyl-4H-pyran-2-carboxylate was hydrolysed to the acid (mp 204°–206° C. with decomposition), by the method described in Example 29. A stirred suspension of this acid (3.6 g) in dry benzene (40 ml) and thionyl chloride (7.7 ml) was heated under reflux for 12 hours and the resulting clear solution was evaporated under vacuum. The residual oil was twice dissolved in dry benzene and re-evaporated to give crude acid chloride which was reacted with butylamine (1.5 ml) in dry pyridine by the method described in Example 35 to give the title product (mp 149°–151° C.).

EXAMPLE 40

5-(4-Methoxyphenyl)-4-oxo-4H-pyran-2-carboxamide

Cold concentrated ammonia solution (30%, 80 ml) was added to a stirred suspension of ethyl 5-(4-methoxyphenyl)-4-oxo-4H-pyran-2-carboxylate (12.4 g) in ethanol (120 ml) at 5°–10° C. The mixture was stirred for a further 30 minutes at 0°–5° C. then the solid title product was washed with water and dried (mp 262°–263° C. with decomposition).

EXAMPLE 41

5-(4-Methoxyphenyl)-4-oxo-4H-pyran-2-carbonitrile

A suspension of 5-(4-methoxyphenyl)-4-oxo-4H-pyran-2-carboxamide (8.0 g) and triphenyl phosphine (17.1 g) in carbon tetrachloride (80 ml), methylene chloride (160 ml) and triethylamine (4.55 ml) was stirred for 3½ hours at room temperature. 2 N Hydrochloric acid (100 ml) was added to the stirred mixture with cooling, then the solvent layer was washed with water, dried, and evaporated. The solid residue was crystallised from chloroform-petroleum spirit (60°–80° C.) to give the title product (mp 165°–167° C.).

EXAMPLE 42

4-Oxo-5-phenyl-4H-pyran-2-carbonitrile

Concentrated ammonia solution (40 ml) was added to a stirred suspension of ethyl 4-oxo-5-phenyl-4H-pyran-2-carboxylate (4.8 g) in ethanol (40 ml) at 10°–15° C. The mixture was then stirred for 30 minutes at 10°–15° C. Then the solid product was recrystallised from dimethylformamide-ethanol to give 4-oxo-5-phenyl-4H-pyran-2-carboxamide (mp 245°–248° with decomposition).

A suspension of this amide (3.5 g) and triphenylphosphine (8.54 g) in carbon tetrachloride (10 ml), methylene chloride (20 ml) and triethylamine (2.3 ml) was stirred for 4 hours at room temperature. Ice (60 g) and 2 N hydrochloric acid (30 ml) were added, followed by sufficient chloroform to dissolve all the solid material. The solvent layer was washed with water, dried and evaporated, and the residue was crystallised from chloroform-petroleum spirit (60°–80° C.) and then from ethanol to give the title product (mp 177°–179° C.).

EXAMPLE 43

5-Phenyl-2-tetrazol-5-yl-4H-pyran-4-one

A mixture of 4-oxo-5-phenyl-4H-pyran-2-carbonitrile (2.0 g), sodium azide (1.0 g) and ammonium chloride (0.8 g) in dimethylformamide (20 ml) was stirred at room temperature for an hour. Ice (20 g) was added and the clear solution was acidified with 2 N hydrochloric acid (20 ml) giving a pale solid which was recrystallised from ethanol to give the title product (mp 237°–238° C. with decomposition).

EXAMPLE 44

5-(4-Methoxyphenyl)-2-tetrazol-5-yl-4H-pyran-4-one

This compound was prepared by the method described in Example 43 (mp 242°–245° C. with decomposition).

EXAMPLE 45

Ethyl 5-(2-hydroxyphenyl)-4-oxo-4H-pyran-2-carboxylate

Boron tribromide (3.0 ml) was added dropwise to a stirred solution of ethyl 5-(2-methoxyphenyl)-4-oxo-4H-pyran-2-carboxylate (3.2 g) in methylene chloride (100 ml) at 5°–10° C. The mixture was stirred for 2 hours at room temperature, then cooled to 5° C. and carefully diluted with water (50 ml). The solid title product was recrystallised from ethanol (mp 187°–189° C.).

EXAMPLE 46

Ethyl 5-(4-hydroxyphenoxy)-4-oxo-4H-pyran-2-carboxylate

Ethyl 5-(4-methoxyphenoxy)-4-oxo-4H-pyran-2-carboxylate (mp 106°–107° C.) was prepared by the method described in Example 17 and the methoxy group was cleaved by the method described in Example 45 to give the title product (mp 206°–208° C.).

EXAMPLE 47

Ethyl 5-(2-hydroxyphenoxy)-4-oxo-4H-pyran-2-carboxylate

This compound was prepared by a method similar to that described in Example 45 (mp 111°–113° C.).

EXAMPLE 48

5-(4-Hydroxyphenoxy)-4-oxo-4H-pyran-2-carboxylic acid

Boron tribromide (8.8 ml) was added dropwise to a stirred solution of ethyl 5-(4-methoxyphenoxy)-4-oxo-4H-pyran-2-carboxylate (4.35 g) in methylene chloride (50 ml) causing gentle reflux. The solution was heated under reflux for a further 2 hours, then cooled and carefully diluted with water (25 ml). The solid title product was recrystallised from water (mp 257°–258° C. with decomposition).

EXAMPLE 49

5-(2-Hydroxyphenoxy)-4-oxo-4H-pyran-2-carboxylic acid

This compound was prepared by the method described in Example 48 (mp 193°–194° C. with decomposition).

EXAMPLE 50

5-(4-Methoxybenzoyl)-4-oxo-4H-pyran-2-carboxylic acid

Treatment of ethyl 5-(4-methoxybenzoyl)-4-oxo-4H-pyran-2-carboxylate with boron tribromide under the conditions described in Example 45 caused preferential cleavage of the ester group to give the title product (mp 185°–190° C. with decomposition).

EXAMPLE 51

3-(3,4-Dimethoxyphenyl)-4-dimethylamino-3-buten-2-one

This compound was prepared by the method described in Example 1 (mp 94° C.).

EXAMPLE 52

Ethyl 5-(3,4-dimethoxyphenyl)-4-oxo-4H-pyran-2-carboxylate

This compound was prepared by the method described in Example 17 (mp 141°–143° C.).

EXAMPLE 53

5-(3,4-Dimethoxyphenyl)-4-oxo-4H-pyran-2-carboxylic acid

This compound was prepared by the method described in Example 29 (mp 210°–212° C. with decomposition).

EXAMPLE 54

Ethyl 5-(3,4-dihydroxyphenyl)-4-oxo-4H-pyran-2-carboxylate

This compound was prepared by the method described in Example 45 (mp 206°–208° C.).

EXAMPLE 55

5-(3,4-Dihydroxyphenyl)-4-oxo-4H-pyran-2-carboxylic acid

This compound was prepared by the method described in Example 29 (mp 284°–285° C. with decomposition).

EXAMPLE 56

5-(3,4-Dimethoxyphenyl)-N-methyl-4-oxo-4H-pyran-2-carboxamide 5-(3,4-Dimethoxyphenyl)-4-oxo-4H-pyran-2-carboxylic acid chloride (mp 130° C.) was prepared and reacted with methylamine by the method described in Example 35 to give the title product (mp 213°–215° C.).

EXAMPLE 57

5-(3,4-Dibenzyloxyphenyl)-4-oxo-4H-pyran-2-carboxylic acid

A mixture of ethyl 5-(3,4-dihydroxyphenyl)-4-oxo-4H-pyran-2-carboxylate (3.0 g), anhydrous potassium carbonate (6.0 g) and benzyl bromide (3.0 ml) in dry DMF (30 ml) was stirred at room temperature for 2 hours and then filtered. The filtrate was cooled, acidified with 2 N hydrochloric acid (20 ml) and diluted with water (80 ml). The solid product was recrystallised from ethanol to give ethyl 5-(3,4-dibenzyloxyphenyl)-4-oxo-4H-pyran-2-carboxylate (mp 122°–125° C.).

A stirred solution of this ethyl ester (7.5 g) and dry lithium iodide (15 g) in dry DMF (120 ml) under nitrogen was heated on an oil bath at 165° to 170° C. for 6 hours. The solution was cooled and acidified with N hydrochloric acid (500 ml) and the solid product was recrystallised from ethanol to give the title product (mp 206°–208° C.).

EXAMPLE 58

Ethyl 5-(4-t-butylbenzoyl)-4-oxo-4H-pyran-2-carboxylate 3-(4-t-Butylbenzoyl)-4-dimethylamino-3-buten-2-one was prepared by the method described in Example 16 and used without purification to prepare the title compound (mp 82°–85° C.) by the method described in Example 17.

EXAMPLE 59

5-(4-t-Butylbenzoyl)-4-oxo-4H-pyran-2-carboxylic acid

This compound was prepared by cleavage of the ethyl ester as described in Example 48, (mp 133°–145° C.).

EXAMPLE 60

3-(4-t-Butylphenoxy)-4-dimethylamino-3-buten-2-one

This compound was prepared by the method described in Example 1 (mp 98° C.).

EXAMPLE 61

5-(4-t-Butylphenoxy)-4-oxo-4H-pyran-2-carboxylic acid

Ethyl 5-(4-t-butylphenoxy)-4-oxo-4H-pyran-2-carboxylate (mp 108°–110° C.), was prepared by the method described in Example 17 and hydrolysed as described in Example 29 to give the title product (mp 190°–193° C. with decomposition).

EXAMPLE 62

3-[4(Cyclohexyl)phenoxy]-4-dimethylamino-3-buten-2-one

Freshly distilled chloroacetone (31 ml) was added to a solution of sodium iodide (1.0 g) in dry acetone (50 ml). The mixture was allowed to stand for 1 hour at room temperature and then added over 1 hour to a stirred, refluxing mixture of 4-(cyclohexyl)phenol (52.8 g) and anhydrous potassium carbonate (52 g) in dry acetone (100 ml). The stirred mixture was heated under reflux for a further 5 hours, filtered and evaporated to a brown oil which crystallised from ether-petroleum spirit (40°–60° C.) to give 1-[4-(cyclohexyl)phenoxy]-2-propanone (mp 58° C.).

The title compound was prepared from this ketone by the method described in Example 1 (mp 137° C.).

EXAMPLE 63

5-[4-(Cyclohexyl)phenoxy]-4-oxo-4H-pyran-2-carboxylic acid

Ethyl 5-[4-(cyclohexyl)phenoxy]-4-oxo-4H-pyran-2-carboxylate (mp 159° C.), was prepared by the method described in Example 17 and hydrolysed as described in Example 29 to give the title product (mp 187°–190° C.).

EXAMPLE 64

5-(4-Butylphenyl)-4-oxo-4H-pyran-2-carboxylic acid

A stirred solution of 4-butylbenzaldehyde (13.5 g), nitroethane (9.0 ml) and butylamine (1.6 ml) in ethanol (20 ml) was heated under reflux for 6 hours and evaporated. The residue was distilled under vacuum to give 1-(4-butylphenyl)-2-nitropropene (bp 124°–125° C./0.15 mm).

Concentrated hydrochloric acid (6.5 ml) was added in small portions over 6 hours to a stirred mixture of this nitropropene (7.6 g), iron powder (13.6 g), and ferric chloride (0.1 g) in water (50 ml) whilst heating under reflux. The mixture was steam-distilled and the distillate extracted with ether. The extract was dried and evaporated and the residue was distilled under vacuum to give 1-(4-butylphenyl)-2-propanone.

This ketone (4.6 g) was reacted with dimethylformamide dimethyl acetal (4.0 ml) as described in Example 1 to give 3-(4-butylphenyl)-4-dimethylamino-3-buten-2-one which was used without purification to prepare ethyl 5-(4-butylphenyl)-4-oxo-4H-pyran-2-carboxylate (mp 65° C.), by the method described in Example 17.

This ester was hydrolysed by the method described in Example 29 to give the title product (mp 193°–195° C.).

EXAMPLE 65

Ethyl 3-bromo-4-oxo-5-phenyl-4H-pyran-2-carboxylate

A suspension of sodium ethoxide was prepared by addition of ethanol (1.6 ml) to a stirred suspension of sodium hydride (1.3 g 50% dispersion, washed with petroleum spirit 40°–60° C.) in ether (50 ml) under nitrogen. A solution of 4-dimethylamino-3-phenyl-3-buten-2-one (4.8 g) and diethyl oxalate (5.2 ml) in ether (50 ml) was added to the stirred sodium ethoxide suspension at 5° to 10° C. and the resulting clear solution was stirred for 2 hours at room temperature, then cooled and treated with glacial acetic acid (2.5 ml) and water (50 ml). Ethyl acetate was added to dissolve the solid which formed and the solvent layer was washed with water, dried, and evaporated. The solid residue was recrystallised from ethyl acetate-petroleum spirit (60°–80° C.) to give ethyl 6-dimethylamino-2,4-dioxo-5-phenyl-5-hexenoate (mp 110° C.).

A solution of bromine (0.73 ml) in chloroform (10 ml) was added dropwise to a stirred solution of this hexenoate (4.1 g) in chloroform (50 ml) at −20° C. to −25° C. The solution was stirred for 1½ hours at room temperature, washed with water and evaporated. The residual solid was crystallised from ethanol-water to give the title product (mp 134° C.).

The following Examples illustrate pharmaceutical formulations containing compounds of formula (I). The active ingredient used was ethyl 4-oxo-5-phenyl-4H-pyran-2-carboxylate. However this compound can be replaced by other active solid compounds of the invention.

EXAMPLE 66

Tablets each containing 50 mg of active ingredient were made up as follows:

| | |
|---|---|
| Active ingredient | 50 mg |
| Starch | 200 mg |
| Lactose | 200 mg |
| Polyvinylpyrrolidone (as 10% solution in water) | 20 mg |
| Sodium starch glycolate | 20 mg |
| Magnesium stearate | 10 mg |
| TOTAL | 500 mg |

The starch, lactose and active ingredient were passed through a sieve and thoroughly mixed. The solution of polyvinylpyrrolidone was mixed with the resultant mixture and the combination passed through a No. 12 mesh B.S. sieve. The granules so produced were dried at approximately 55° C. and passed through a No. 16 mesh B.S. sieve. The magnesium stearate and sodium starch glycolate, previously passed through a No. 60 mesh B.S. sieve, were then added to the granules which, after mixing, were compressed on a tablet machine to yield tablets each weighing 500 mg.

EXAMPLE 67

Capsules each containing 50 mg of medicament were made as follows:

| Active ingredient | 50 mg |
| --- | --- |
| Starch | 42 mg |
| Lactose | 45 mg |
| Magnesium stearate | 3 mg |
| TOTAL | 140 mg |

The lactose, starch, magnesium stearate and active ingredient were passed through a No. 44 mesh B.S. sieve and filled into hard gelatin capsules in 140 mg quantities.

EXAMPLE 68

Suppositories each containing 25 mg of active ingredient were made as follows:

| Active ingredient | 50 mg |
| --- | --- |
| Saturated fatty acid glycerides to | 2,000 mg |

The active ingredient was passed through a No. 60 mesh B.S. sieve and suspended in the saturated fatty acid glycerides previously melted using the minimum heat necessary. The mixture was then poured into a suppository mould of nominal 2 g capacity and allowed to cool.

We claim:

1. A compound of the formula

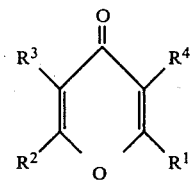

in which $R^1$ is $COOR^5$, $CONHR^5$, cyano, 5-tetrazolyl or 5-tetrazolylaminocarbonyl, where $R^5$ is hydrogen or $C_{1-6}$ alkyl; $R^2$ is hydrogen or $C_{1-6}$ alkyl; $R^3$ is a group of the formula $$R^6-(Z)_m-$$

where m is 0 or 1, Z is O, S, SO, $SO_2$ or CO, and $R^6$ is phenyl optionally substituted by one or more group selected from halogen, $C_{1-4}$ alkyl, $C_{3-6}$ cycloalkyl, $C_{1-4}$ alkoxy, benzyloxy, hydroxy, nitro, $C_{1-4}$ alkylthio, $C_{1-4}$ alkylsulphinyl, $C_{1-4}$ alkylsulphonyl, amino and $NHR^7$ where $R^7$ is $C_{2-6}$ acyl; and $R^4$ is hydrogen, $C_{1-6}$ alkyl or halogen; and pharmaceutically acceptable salts thereof.

2. A compound according to claim 1 in which $R^4$ is hydrogen or $C_{1-6}$ alkyl.

3. A compound according to claim 2 in which $R^1$ is $COOR^5$, $CONHR^5$ or 5-tetrazolyl.

4. A compound according to claim 2 in which $R^3$ is of the formula $$R^6-(Z)_m-$$

where m is 0 or m is 1 and Z is O or CO.

5. A compound according to claim 2 in which $R^1$ is $COOR^5$ or $CONHR^5$ where $R^5$ is hydrogen or $C_{1-6}$ alkyl, $R^2$ is hydrogen, $R^3$ is a group of the formula $R^6-(Z)_m-$ where m is 0 or 1, Z is O, S or CO and $R^6$ is phenyl optionally substituted by halogen, methyl, methoxy or hydroxy.

6. A pharmaceutical formulation in unit dosage form adapted for administration to treat an immediate hypersensitivity condition of the type represented by asthma which comprises per dosage unit an effective amount of a compound according to claim 1, or a pharmaceutically-acceptable salt thereof, associated with a pharmaceutically-acceptable carrier therefor.

7. A pharmaceutical formulation in unit dosage form adapted for administration to treat an immediate hypersensitivity condition of the type represented by asthma which comprises per dosage unit an effective amount of a compound according to claim 2, or a pharmaceutically-acceptable salt thereof, associated with a pharmaceutically-acceptable carrier therefor.

8. A method of treating an animal, including a human, susceptible to or suffering from an immediate hypersensitivity condition of the type represented by asthma, which comprises administering a effective amount of a compound as defined in claim 1.

9. A method of treating an animal, including a human, susceptible to or suffering from an immediate hypersensitivity condition of the type represented by asthma, which comprises administering an effective amount of a compound as defined in claim 2.

* * * * *